United States Patent [19]

Larsen

[11] 4,144,753

[45] Mar. 20, 1979

[54] CIRCUIT ARRANGEMENT FOR DETERMINING PHYSICAL PARAMETERS OF FLOWING MEDIA BY THE ULTRASONIC METHOD

[75] Inventor: Poul M. Larsen, Sonderborg, Denmark

[73] Assignee: Danfoss A/S, Nordborg, Denmark

[21] Appl. No.: 823,995

[22] Filed: Aug. 12, 1977

[30] Foreign Application Priority Data

Aug. 18, 1976 [DE] Fed. Rep. of Germany ....... 2637107

[51] Int. Cl.² .............................................. G01F 1/66
[52] U.S. Cl. ..................................... 73/194 A; 73/597
[58] Field of Search ............................. 73/194 A, 597

[56] References Cited

U.S. PATENT DOCUMENTS 4,022,058  5/1977  Brown ............................... 73/597 X

*Primary Examiner*—Charles A. Ruehl
*Attorney, Agent, or Firm*—Wayne B. Easton

[57] ABSTRACT

The invention relates to a circuit for determining the arrival time of an ultrasonic signal. The circuit includes a differentiator for transforming an ultrasonic signal to a substantially linearly increasing signal, and a threshold value detector for transforming the linearly increasing signal to an arrival delay signal. A phase detector in the form of a D-type flip-flop determines the phase position of the arrival delay signal relative to a reference signal. The phase detector generates early signals on early arrival of the delay signal and late signals on late arrival of the delay signal. A regulator integrator is provided between the phase detector and the differentiator for producing an output voltage for altering the delay period of the arrival delay signal responsive to the phase position of the delay signal. Resetting apparatus is provided between the regulator integrator and the phase detector for resetting the integrator when the output voltage reaches a predetermined maximum or minimum value to cause the output voltage to return to zero. The resetting apparatus includes hysteresis for maintaining resetting signals until the output voltage is substantially zero.

6 Claims, 2 Drawing Figures

CIRCUIT ARRANGEMENT FOR DETERMINING PHYSICAL PARAMETERS OF FLOWING MEDIA BY THE ULTRASONIC METHOD

By means of this circuit arrangement, the arrival time of the ultrasonic signal can be determined with extraordinary accuracy so that a correspondingly high accuracy is also obtained for the physical parameters to be measured. A decisive contributing factor in this respect is that the arrival delay signal follows one flank of the rectangular signal and thus the next zero passage of the rectangular signal can be determined with considerable certainty.

The invention is based on the problem to improve a circuit arrangement of this kind in such a way that its manner of operation is influenced as little as possible by temporary interruptions in the received ultrasonic signal.

This problem is solved according to the invention by a resetting apparatus which responds when the output voltage of the integrator reaches a predetermined positive and/or negative limiting value and then brings the output voltage towards zero.

When the received ultrasonic signal is interrupted or interfered with, e.g. through interference in the electrical system or by air occlusions in a flowing liquid, portions of the rectangular signal and also the arrival delay signal will also be omitted. It is therefore no longer possible to make the arrival delay signal follow the flank of the rectangular signal. The input signals then fed to the integrator are of a haphazard nature and can for example correspond to the last correct early or late signal given out or both have the same value continuously but with a somewhat different voltage. In any case, there is a danger that the integrator will be operated up to its saturation range by these input signals. As soon as normal conditions obtain again, it is extremely difficult or even impossible to bring the arrival delay signal back towards the flank of the rectangular signal.

By using the resetting apparatus, one prevents the integrator from being brought to the saturation range under all circumstances. Instead, the integrating direction is reversed before the saturation range is reached. This ensures that on resumption of normal operation the integrator will be in an operating range in which the flank of the rectangular voltage is located and in which it can integrate in both directions with hindrance and thereby make the arrival delay signal follow.

With particular advantage a signal generator is provided which feeds to the integrator a predetermined input signal that changes the output voltage of the integrator towards zero, and that on response the resetting apparatus produces a resetting signal which makes the signal generator operative for a certain time. This reverses the integrating direction in a simple manner and brings the output voltage towards zero.

In a preferred example, the resetting apparatus comprises two branches of which the first gives out a first resetting signal on falling below a negative limiting value and the second gives out a second resetting signal on exceeding a positive limiting value, the switching apparatus applies input pulses to the inverting input of the integrator on the occurrence of the one resetting signal and input pulses to the non-inverting input on the occurrence of the other resetting signal. In this way the positive and the negative saturation range is excluded.

Preferably, provision is made for the signal generator to be operative during the period of the resetting signal and the resetting apparatus includes a response hysteresis by reason of which the resetting signal is maintained until the output voltage of the integrator is substantially zero. The result of this is that the integrator is basically returned to about the middle of its regulating range independently of other influences after it has reached its limits.

The signal generator may comprise the phase detector if this has at least one additional input for a resetting signal and, on the occurrence of which, is only adapted to give out early or late signals. One then requires no additional structural unit for the signal generator.

If the phase detector comprises a device of which the preparatory input or data input is supplied with the rectangular signal and the beat input is supplied with the arrival delay signal, and at the two outputs the early and late signals are given out, this can be achieved with a D-flip-flop which has a clear control preset control inputs to which one of the two resetting signals can be fed.

It is recommended that each branch of the resetting apparatus be provided with a comparator with hysteresis in the form of a differential amplifier with feedback, of which one input is fed with the output voltage of the integrator and the other input with a fixed reference signal. The positive and negative operating range of the integrator are then separately monitored in a simple manner.

The invention will now be described in more detail with reference to the example illustrated in the drawing, in which.

Figure 1:
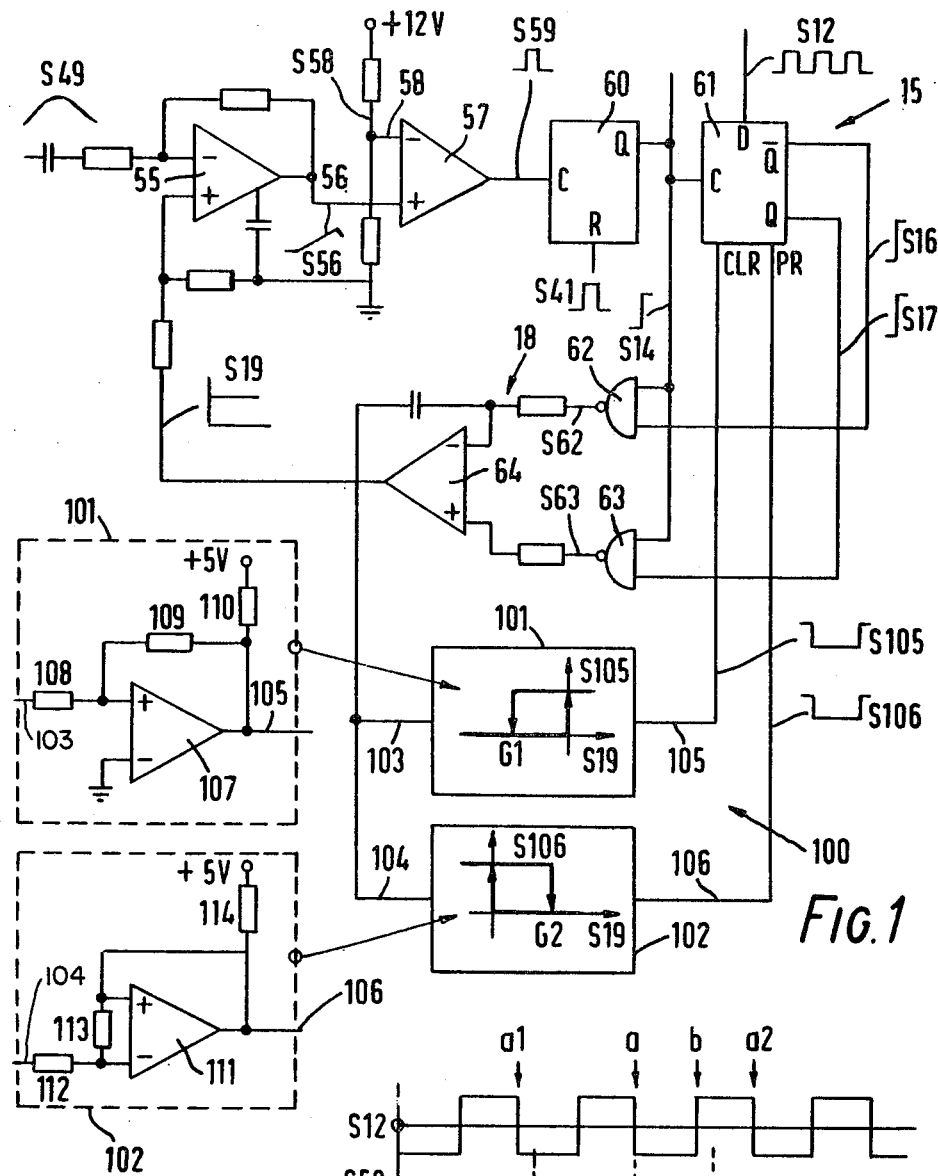
FIG. 1 is a circuit arrangement of an embodiment of the invention.

Referring to the drawing, a received ultrasonic signal is converted to a rectangular signal S12 by amplification. Also, an enveloping curve S49 is produced by rectification and smoothing and fed to a differentiator 55. The latter preferably consists of a ramp amplifier of which the 'slew rate' (ascending velocity of the output signal) is limited. Consequently a signal S56 is emitted at the output 56 that has a constant ascending velocity. This output signal S56 is compared in a threshold value detector 57 with a fixed threshold value supplied through the input 58. On reaching this threshold value, a threshold value signal S59 is applied to the setting input C of a D-flip-flop 60 which consequently emits an arrival delay signal S14 at its output Q until resetting is effected by a resetting signal S41.

The arrival delay signal S14 is fed to the clock input C of a D-flip-flop 61 of which the preparatory input D is fed with the rectangular signal S12. Consequently an early signal S16 appears at the output $\bar{Q}$ and a late signal S17 at the output Q which are linked with the arrival delay signal S14 in NAND elements 62 or 63 and can therefore be fed to an integrator 64 as pulses S62 and S63 of substantially constant charge. The early signal pulses S62 are fed to the inverting input of the integrator 64 and the late signal pulses S63 are fed to the non-inverting input. When the arrival delay signal S14 does not accurately coincide with the rear edge of an impulse of the rectangular signal S12, the number of early or late signals predominates and the size of the control voltage S19 is changed at the output of the integrator 64. This output voltage is fed to the non-inverting input of the ramp amplifier 55 with the result that the output voltage S56 is displaced upwardly or downwardly parallel to itself. This changes the point of intersection with the threshold value S58 and thus the instant of the threshold value signal S59 and the arrival delay signal S14 until the last-mentioned signal again coincides with the descending flank of the rectangular signal S12. The D-flipflop 61 therefore forms a phase detector with the aid of which the regulating apparatus 18 formed by the integrator 64 is controlled in such a way that in a zero point detector (not shown) the zero passage of the rectangular signal S12 following the occurrence of the arrival delay signal can be determined with high accuracy.

Figure 2:
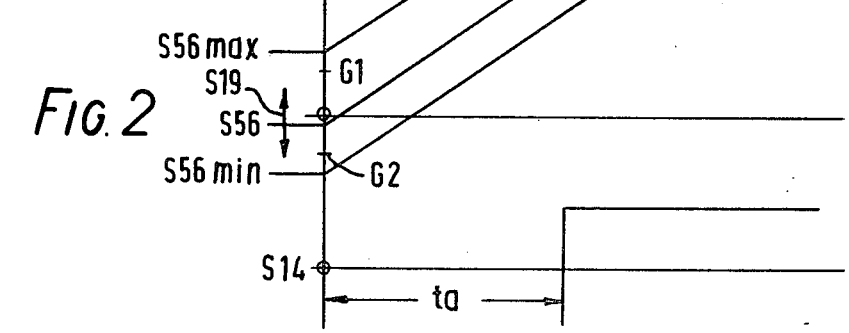
FIG. 2 shows several signals referenced relative to time.

FIG. 2 again shows this manner of operation. The arrival delay signal S14 is controlled with respect to the delay period ta in such a way that it coincides as accurately as possible with the descending flank a of the rectangular signal S12. The next zero passage determined by the ascending flank b can then be accurately detected. The ramp signal S56 is transposed upwardly or downwardly with the aid of the control voltage S19 in the direction of the arrow so that the point of intersection with the threshold value S58 that determines the arrival delay signal S14 coincides with a flank a.

If through any error the rectangular signal S12 and the arrival delay signal S14 are absent, the usual comparison is not possible. The phase detector 15 will not be operated; the NAND elements continuously emit output signals S62 and S63 with the value 1. By reason of voltage differences for these signals, the integrator goes from the last available integrating value to a terminal position that is determined by its saturation. These two conditions are designated as S56 max and S56 min in FIG. 2.

If, now, the ultrasonic signal is again received normally, the rectangular signal S12 is present and the arrival delay signal S14 appears, the phase detector 15 would emit late signals S17 in the case of S56 max so that the adjacent descending flank a1 is reached; this is not possible because the integrator 64 is already in the saturation condition. In the case of S56 min, the phase detector 15 seeks to find the time connection to the descending flank a2 by emitting early signals; this is also not possible because the integrator 64 is in the saturation condition.

To avoid this danger, the invention ensures that the output point of the signal S56 defined by the output signal S19 cannot fall below a lower limiting value G1 and not exceed an upper limiting value G2. Instead, when this limiting value is reached, the integrating direction of the integrator 64 is so controlled that the output voltage S19 moves towards zero. The circuit now to be described serves this purpose.

Said circuit comprises a resetting apparatus 100 comprising two branches 101 and 102. The inputs 103 and 104 of both branches are fed with the control signal S19, i.e. the output voltage of the integrator 64. The output 105 of the first branch 101 is connected to a clear control input CLR and the output 106 of the second branch 102 to a preset control input PR of the D-flip-flop 61. The corresponding resetting signals S105 and S106 are normally available as a voltage which, however, becomes zero to influence the D-flip-flop 61.

Both branches have hysteresis. In the branch 101 the resetting signal S105 becomes zero when the control voltage S19 falls below the limiting value, G2. The resetting signal S105 then remains zero until the control voltage S19 has become zero. It then returns to its normal value. Similarly, the resetting signal 106 becomes zero when the control voltage S19 exceeds the limiting value G1. It retains this value until the control voltage S19 has become zero.

An example for the construction of such a branch 101 and 102 is illustrated in the blocks shown in FIG. 1 in broken lines. In the branch 101 a differential amplifier 107 connected as an amplifier with an open collector output is shown with the inverting input applied to earth. The non-inverting input is connected to the input 103 by way of a resistor 108. In addition, a feedback with a resistor 109 is provided. The output is also connected to a limiting value of +5V by way of a resistor 110. As soon as the input voltage falls below a value of −5V, the resetting signal S105 becomes zero. Because of the feedback, this condition is maintained until the voltage at the input has again reached zero. A differential amplifier 111 of which the inverting input is connected to the input 104 by way of resistor 112 is provided in the branch 102. The non-inverting input is connected by way of a second resistor 113 to the inverting input and directly to the output 106 which again lies by way of a resistor 114 at a fixed voltage determining the limiting value G2. When the input voltage has reached ±5V, the amplifier 111 switches its output to zero. Resetting is possible only when there is again 0V at the input 104.

By means of the resetting signals S105 and S106, the D-flip-flop 61 becomes part of a signal generator which permits predetermined input signals to be fed to the integrator 64. When the clear control input CLR has the signal 0 fed to it, the output $\bar{Q}$ for the early signals S16 is preprogrammed to 1 and the output Q for the late signals S17 to 0. Each time an arrival delay signal S14 appears, the NAND element 62 emits a signal S62 in the same way as on the presence of an early signal S16. Because of the signal S62, the control voltage S19 falls until it has reached the value 0. The same applies when the resetting signal S106 becomes 0 at the preset control input PR. In that case the output Q is preprogrammed to 1 and the output $\bar{Q}$ to 0 and on each occurrence of the arrival delay signal S14 a signal S63 appears at the output of the NAND element 63 in the same way as on the presence of a late signal S17, whereby the control voltage S19 is raised until it has again reached the value 0. If the resetting signals S105 and S106 then again have their normal value, the D-flip-flop 61 will operate in the usual manner.

By appropriately dimensioning the limiting values G1 and G2, the integrator 64 is prevented from reaching the saturation condition so that on resumption of normal conditions proper operation is possible. One can even achieve that the point of intersection of the signal S56 with the threshold value S58 will always be within limits within which it is possible again to follow the originally selected flank a. This is favourable when no delay compensation is provided for permitting a change of flanks.

if the inteference has not yet been eliminated when the resetting signals have become inoperative, it may happen that the control voltage S19 again increases to a limiting value and the integration direction is reversed once more or several times.

I claim:

1. A circuit for determining the arrival time of an ultrasonic signal, comprising, means for transforming said ultrasonic signal to a substantially linearly increasing signal, threshold value detector means for transforming said linearly increasing signal to an arrival delay signal, phase detector means for determining the phase position of said arrival delay signal relative to a reference signal, said phase detector means generating early signals on early arrival of said delay signal and generating late signals on late arrival of said delay signal, regulator integrator means between said phase detector means and said threshold value detector means producing an output voltage for altering the delay period of said arrival delay signal responsive to the phase position of said delay signal, resetting means between said regulator integrator means and said phase detector means for resetting said integrator means to zero when said output voltage reaches a predetermined maximum or minimum value to cause said output voltage to return to zero.

2. A circuit according to claim 1 wherein said resetting means has two branches for generating first and second resetting signals respectively when said output voltage exceeds a positive limiting value or falls below a negative limiting value, said phase detector means applying input pulses to either the inverting or noninverting inputs of said integrator means on the occurrence of one or the other of said resetting branches being activated.

3. A circuit according to claim 2 wherein each of said branches has comparator means with hysteresis in the form of a differential amplifier with feedback.

4. A circuit according to claim 1 wherein said resetting means includes hysteresis means for maintaining resetting signals until said output voltage is substantially zero.

5. A circuit according to claim 2 wherein said phase detector means includes a flip-flop with setting and clearing inputs connected respectively to said branches.

6. A circuit according to claim 5 wherein said flip-flop is a D-type with data a clock inputs, said reference signal being applied to said data input and said delay signal being applied to said clock input.

* * * * *